US007135607B1

(12) United States Patent
Nakamura et al.

(10) Patent No.: US 7,135,607 B1
(45) Date of Patent: Nov. 14, 2006

(54) GOODPASTURE'S SYNDROME MODEL MOUSE

(75) Inventors: Akira Nakamura, Sendai (JP); Toshihiro Nukiwa, Sendai (JP); Toshiyuki Takai, Sendai (JP)

(73) Assignee: Japan Science and Technology Agency, Kawaguchi (JP)

( * ) Notice: Subject to any disclaimer, the term of this patent is extended or adjusted under 35 U.S.C. 154(b) by 364 days.

(21) Appl. No.: 10/009,950

(22) PCT Filed: Jun. 23, 2000

(86) PCT No.: PCT/JP00/04132

§ 371 (c)(1),
(2), (4) Date: Dec. 14, 2001

(87) PCT Pub. No.: WO01/00015

PCT Pub. Date: Jan. 4, 2001

(30) Foreign Application Priority Data

Jun. 25, 1999 (JP) ............................... H11-180600

(51) Int. Cl.
*G01N 33/00* (2006.01)
*A01K 67/33* (2006.01)
*A01K 67/027* (2006.01)
*A01K 67/00* (2006.01)

(52) U.S. Cl. .................. 800/3; 800/18; 800/9
(58) Field of Classification Search .................... 800/8, 800/18, 3
See application file for complete search history.

(56) References Cited

FOREIGN PATENT DOCUMENTS

JP          8-289699          11/1996

OTHER PUBLICATIONS

Lederman, 2000, Embryonic stem cells and gene targeting, Experimental Physiology, vol. 85, pp. 603-613.*
Campbell and Wilmut, 1997, Totipotency or multipotency of cultured cells: applications and progress, Theriogenology, vol. 47, pp. 63-72.*
Griffiths, 1998, Current comcepts of PLP and its role in the nervous system, Microscopy Research and Technique, vol. 41, pp. 344-358.*
Leonard, 1995, Role of the common cytokine receptor gamma chain in cytokine signaling and lymphoid development, Immunological Reviews, vol. 148, pp. 97-114.*
Kalluri, R et al. 1997, J Clin Invest, 100:2263-2275.*
Kalluri, R et al. 1995, J Am Soc Nephrol, 6:1178-1185.*
Lerner et al., "The Role Of Anti-Glomerular Basement Membrane Antibody In the Pathogenesis Of Human Glomerulonephritis" The Journal of Experimental Medicine, vol. 126, pp. 989-1004, plates 72-76, (1967).
Gunwar et al., "Alveolar Basement Membrane: Molecular Properties of The Noncollagenous Domain (Hexamer) Of Collagen IV And Its Reactivity With Goodpasture Autoanibodies", Am. J. Respair. Cell Mol. Biol., vol. 5, pp. 107-112, (1991).
Fridman et al., "Structural Bases Of Fcγ Receptor Functions", Immunological Reviews, published by Munksgaard, Copenhagen, Denmark, No. 125, pp. 49-76, (1992).
Amiogorena et al., "Cytoplasmic Domain Heterogeneity And Functions of IgG Fc Receptors In B Lymphocytes", Science, vol. 256, pp. 1808-1812, (1992).
Takai et al., "Augmented Humoral And Anaphylactic Responses In Fcγ RII-Deficient Mice", Nature, vol. 379, pp. 346-349, (1996).
Yuasa et al., "Deletion Of Fcγ Receptor IIB Renders H-2bMice Susceptible To Collagen-Induced Arthritis", J. Exp. Med., The Rockefeller University Press, vol. 189(1):187-194, (1999).
Ohmori et al., "Enhancement of Antigen-Induced Interleukin 4 and IgE Production By Specific IgG1 In Murine Lymphocytes", Cellular Immunology, Academic Press, Inc., vol. 145, pp. 299-310, (1992).
Nakamura et al., "Fcγ Receptor IIB-Deficient Mice Develop Goodpasture's Syndrome Upon Immunization With Type IV Collagen: A Novel Murine Model For Autoimmune Glomerular Basement Membrane Diease", J. Exp. Med., The Rockefeller University Press, vol. 191(5):899-905, (2000).
Kalluri et al., "The a3 Chain of Type IV Collagen Induces Autoimmune Goodpasture Syndrome", Proc. Natl. Acad. Sci. USA, Immunology, vol. 91, pp. 6201-6205, (1994).
Reynolds et al., "Experimental Autoimmune Glomerulonephritis (EAG) Induced By Homologous And Heterologous Glomerular Basement Membrane In Two Substrains Of Wistar-Kyoto Rat", Nephrol Dial Transplant, European Renal Association-European Dialysis and Transplant Association, vol. 13:44-52, (1998).
W. Kline Bolton et al., "Goodpasture's Epitope in Development of Experimental Autoimmune Glomerulonephritis in Rat's", Kidney International, vol. 49, (1996), pp. 327-334.

(Continued)

*Primary Examiner*—Anne-Marie Falk
*Assistant Examiner*—Valarie Bertoglio
(74) *Attorney, Agent, or Firm*—Ann S. Hobbs; Robert Kinberg; Venable LLP

(57) ABSTRACT

The present invention provides a non-human model animal of Goodpasture's syndrome that contributes to the treatment of Goodpasture's syndrome where the development of therapy had been delayed due to the lack of adequate disease models, a method for screening a remedy for Goodpasture's syndrome by using the model animal, and a method for diagnosing Goodpasture's syndrome at the early stage. A Goodpasture's syndrome model mouse is constructed by immunizing immunoglobulin Fcγ receptor IIB knockout mouse with type IV collagen, thereby inducing Goodpasture's syndrome. Moreover, a remedy for Goodpasture's syndrome is screened by administration of test substances to the Goodpasture's syndrome model mouse, followed by evaluating the severity of the expression of Goodpasture's syndrome as an index, such as diffuse alveolar hemorrhage, glomerulonephritis, the appearance of antikidney glomerular basement membrane antibody, and the like.

2 Claims, 3 Drawing Sheets

OTHER PUBLICATIONS

Mauro Abbate et al., "Experimental Goodpasture's Syndrome in Wistar-Kyoto Rats Immunized with α3 Chain of Types IV Collagen", Kidney International, vol. 54 (1998), pp. 1550-1561.

Raghu Kalluri, "Goodpasture Syndrome", Kidney International, vol. 55 (1999), pp. 1120-1122.

* cited by examiner

× 100

GOODPASTURE'S SYNDROME MODEL MOUSE

TECHNICAL FIELD

The present invention relates to a non-human model animal of Goodpasture's syndrome, a method for screening a remedy for Goodpasture's syndrome by using the model animal, and a method for diagnosing Goodpasture's syndrome at the early stage.

PRIOR ART

Goodpasture's syndrome, which has the combination of diffuse alveolar hemorrhage, glomerulonephritis, and the appearance of antikidney glomerular basement membrane antibody, is similar as a clinical feature with Wegener's granulomatosis, systemic necrotizing vasculitis, systemic lupus erythematosus (SLE) and the like, and is believed that antibodies common to the kidney glomerular basement membrane and alveolar epithelium basement membrane exist in the patient's serum, which bind to the target tissues and induce lesion of inflammation based on type II hypersensitivity reaction (J. Exp. Med. 126, 989–1004, 1987). Aside from the characteristics of the above-mentioned clinical feature, the diagnosis of Goodpasture's syndrome is made by proving the deposition of immunoglobulin (hereinafter "Ig") on the kidney glomerular basement membrane, where most of the anti basement membrane antibodies belong to the IgG fraction, and in recent years, it has been identified as an autoantibody to a part of the $\alpha_3$ chain of type IV collagen (Cell Mol. Biol. 5, 107–112, 1991).

Moreover, the onset of Goodpasture's syndrome is found in a wide range of age bracket, where without its diagnosis and therapy at the early stage, 80% of the patients die within a year due to the deterioration of nephrosis, and 30% of the patients die due to pulmonary hemorrhage. Recently, therapy at the early stage has enabled to increase the average of saving lives of Goodpasture's syndrome to about 50%, but therapy only with the use of oral steroid agent or oral immunosuppressive drug is insufficient, and using high-dose of predonine pulse therapy is effective for pulmonary hemorrhage. However, pulse therapy is not sufficient for nephrosis, and is said that plasma exchange and high-dose of predonine, with the use of cyclophosphamide at the same time is effective, whereas to serious renal damage, artificial dialysis or renal transplantation is considered.

On the other hand, receptors that recognize and bind to the Fc portion of Ig (hereinafter "FcR") exist on the surface of cells in such as the immune system and the like, and the Fc γ receptor (hereinafter "FcγR") among them, which is a receptor protein that binds specifically to the γ chain of IgG in the body fluid, is classified mainly into three types, type I (CD64 antigen), type II (CD32 antigen), and type III (CD16 antigen), based on the similarity of gene structure. Among these, FcγRII differs from the other FcRs in that it has low affinity to the IgG of the monomer, binds to the polyvalent IgG that has become an immune complex, and is widely expressed in the hemopoietic stem cells including monocytes, macrophages, polymorphonuclear (PMN) leukocytes, mast cells, platelets, some of the T cell lymphocytes and B cell lymphocytes. Moreover, three types of receptors having different gene arrangements, FcγRIIA, FcγRIIB, and FcγRIIC, exist in the FcγRII, and it is also known that each of the chromosomes are positioned in 1q23.

Unlike the other FcRs, the above-mentioned FcγRIIB does not associate with γ chain, and has an amino acid sequence (ITIM: Immunoreceptor Tyrosine-based Inhibition Motif) which transmits supressive signal to the intracellular domain (Immunol. Rev. 125, 49–76, 1992, Science 256, 1808–1812, 1992). In order to elucidate these physiological functions of FcγRIIB, the inventors of the present invention had already constructed FcγRIIB-deficient mouse (Nature 379, 346–349, 1996), and constructed arthritis model mouse which is generated by immunizing FcγRIIB-deficient mice with type II collagen (J. Exp. Med. 189, 187–194, 1999), and autoimmune disease model mouse (Japanese Laid-Open Patent Publication No. 08-289699).

Model animals that are effective in the study on the pathogenesis of Goodpasture's syndrome, where 80% of the patients die within a year due to the deterioration of nephrosis and 30% among the patients die due to pulmonary hemorrhage without its diagnosis and therapy at the early stage, and in the development of therapy for Goodpasture's syndrome, had not been known to the present. An object of the present invention is to present a non-human model animal of Goodpasture's syndrome contributing to the treatment of Goodpasture's syndrome where the development of therapy had been delayed due to the lack of adequate disease models to elucidate its onset mechanism, a method for screening a remedy for Goodpasture's syndrome by using the model animal, and a method for diagnosing Goodpasture's syndrome at the early stage.

SUMMARY OF THE INVENTION

The inventors of the present invention have conducted intensive study to elucidate the physiological functions of FcγRIIB, and have discovered that when a mouse whose function of FcγRIIB gene is deficient on its chromosome, namely, the FcγRIIB knockout mouse, is immunized with type IV collagen, said FcγRIIB knockout mouse indicates diagnostic sign of Goodpasture's syndrome, and thus the present invention has been completed.

The present invention relates to a non-human model animal of Goodpasture's syndrome, especially Goodpasture's syndrome model mouse, which is obtained by immunizing a non-human animal whose function of immunoglobulin Fcγ receptor IIB gene is deficient on its chromosome with type IV collagen or peptide which includes a part of its amino acid sequence.

Moreover, the present invention relates to a method for screening a remedy for Goodpasture's syndrome characterized in that: test substances are administered to a non-human animal whose function of immunoglobulin Fcγ receptor IIB gene is deficient on its chromosome before, after or at the same time it is immunized with type IV collagen; and the severity of the expression of Goodpasture's syndrome as an index is evaluated, a method for screening a remedy for Goodpasture's syndrome characterized in that: test substances are administered to a non-human model animal of Goodpasture's syndrome; and the severity of the expression of Goodpasture's syndrome as an index is evaluated, the above-mentioned method for screening a remedy for Goodpasture's syndrome characterized in that: a comparative evaluation with the wild-type non-human animal used as a control is made when the severity of the expression of Goodpasture's syndrome as an index is evaluated, the above-mentioned method for screening a remedy for Goodpasture's syndrome characterized in that: the expression of Goodpasture's syndrome is at least one among diffuse alveolar hemorrhage, glomerulonephritis, and the appearance of antikidney glomerular basement membrane antibody, and the above-mentioned method for screening a remedy for Goodpasture's syndrome characterized in that: the non-human animal is a mouse.

In addition, the present invention relates to a method for diagnosing Goodpasture's syndrome at the early stage, wherein a Fcγ receptor IIB gene is extracted from human test cells, and is examined whether there is any deficiency in the function of said gene.

BEST MODE FOR CARRYING OUT THE INVENTION

Figure 1:
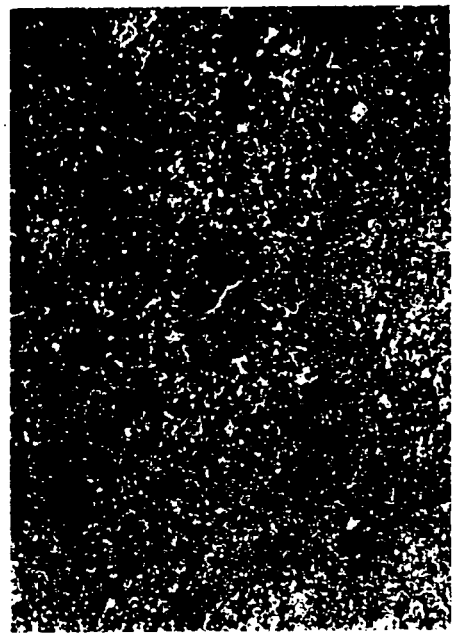
FIG. 1 is a view showing Goodpasture's syndrome-like alveolar hemorrhage by immunization with type IV collagen.
Figure 1:
Figure 1:
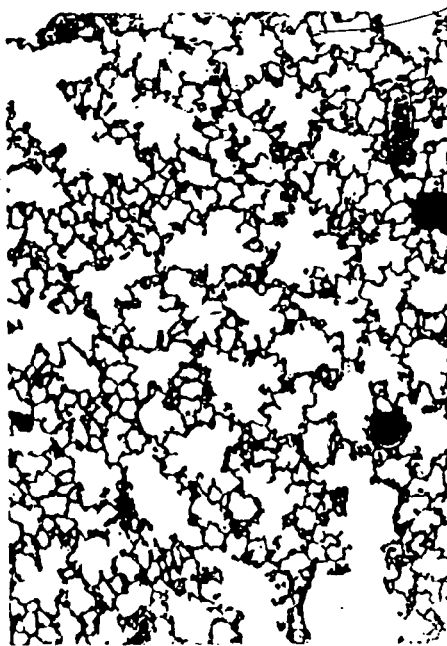
Figure 1:
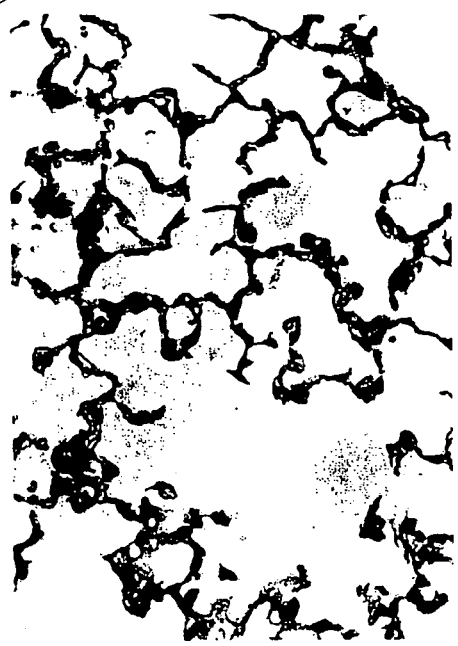

In the present invention, a "non-human animal whose function of FcγRIIB gene is deficient on its chromosome" means a non-human animal whose function of expressing FCγRIIB is impaired by inactivation of endogenous genes of the non-human animal encoding FcγRIIB caused by genetic mutation such as destruction, deficiency, substitution or the like. Specific examples of "non-human animal" in the present invention include a rodent such as a mouse or a rat, but are not limited to these examples.

For example, mouse whose function of FcγRIIB gene is deficient on its chromosome, namely, the FcγRIIB knockout mouse, can be constructed by using the method as previously described (Nature 379, 346–349, 1996) by the present inventors, or the like. Specifically, a gene fragment obtained from a mouse genomic library using methods such as PCR or the like is used to screen the FcγRIIB gene, and the FcγRIIB gene which had been screened is subcloned by using a viral vector or the like, and is determined by DNA sequencing. A fragment that includes $S_2$ exon and $EC_1$ exon of the said clone was substituted with pMC1 neo gene cassette or the like, and a target vector was generated.

The linearized vector was introduced into ES cells by methods such as electroporation or the like, followed by homologous recombination, and ES cells indicating resistance to G418 and the like were selected from said homologous recombinants, and then the clone of said cells were microinjected into the blastocysts of the mice, said blastocysts were returned to the tentative parent mice, and chimeric mice were generated. These chimeric mice were intercrossed with wild-type mice to obtain heterozygous mice, and these heterozygous mice were intercrossed to obtain FcγRIIB knockout mice.

In the present invention, type IV collagen is a specific exemplification of an immunogen used to induce Goodpasture's syndrome to a non-human animal whose function of FcγRIIB gene is deficient on its chromosome, however, anything such as a peptide which includes a part of the amino acid sequence of type IV collagen or the like can be used, as long as Goodpasture's syndrome can be induced to the non-human animal whose function of FcγRIIB gene is deficient on its chromosome.

In the present invention, a "non-human model animal of Goodpasture's syndrome" can be any kind of non-human animal, as long as it is a non-human animal such as a mouse or the like, which has the combination of three diagnostic signs of diffuse alveolar hemorrhage, glomerulonephritis, and the appearance of antikidney glomerular basement membrane antibody. For example, it can be obtained by immunizing a non-human animal whose function of FcγRIIB gene is deficient on its chromosome with type IV collagen.

Examples of methods for screening a remedy for Goodpasture's syndrome in the present invention are: a method in which test substances that are expectants for the remedy for Goodpasture's syndrome are administered to the non-human animal whose function of FcγRIIB gene is deficient on its chromosome before or after Goodpasture's syndrome is induced to the non-human animal by immunization with type IV collagen; or at the same time Goodpasture's syndrome is induced to the non-human animal by immunization with type IV collagen; and the severity of the expression of Goodpasture's syndrome (appearance of diagnostic signs) as an index is evaluated, and a method in which test substances that are expectants for the remedy for Goodpasture's syndrome are administered to the Goodpasture's syndrome non-human model animal; and the severity of the expression of Goodpasture's syndrome as an index is evaluated.

In addition, when evaluating the severity of the expression of Goodpasture's syndrome as an index, a wild-type non-human animal of the same species as the non-human model animal of Goodpasture's syndrome can be used as a control, and a comparative evaluation of the severity of the expression of Goodpasture's syndrome between the non-human model animal of Goodpasture's syndrome and the wild-type non-human animal of the same species used as a control can be made.

As an index of the severity of expression (appearance of diagnostic signs) of Goodpasture's syndrome, at least one among diffuse alveolar hemorrhage in the pulmonary tissues, glomerulonephritis in the renal tissues, and the appearance of antikidney glomerular basement membrane antibody can be favorably exemplificated, including other examples such as the expression of anti basement membrane antibody depositing in the pulmonary alveoli, serum creatinine level, the glomus filtration value, or the like. Evaluating at least one of these indexes can screen the remedy for Goodpasture's syndrome.

In the present invention, a specific method for diagnosing Goodpasture's syndrome at the early stage is to extract FcγRIIB gene from human test cells, and examine whether there is any deficiency in the function of said gene. Examples of human test cells used as Fc RIIB gene source are macrophages, mast cells, B cells, dendritic cells and the like, and an example of a method for examining whether there is any deficiency in the function of FcγRIIB gene is to express the cloned FcγRIIB gene in the human cell line by ordinary method, and examine the function of FcγRIIB of the expression product, such as the binding to IgG immune complex. Onset of Goodpasture's syndrome is possible when there is a deficiency in the function of FcγRIIB in the expression product, and as mentioned above, a method for diagnosing Goodpasture's syndrome at the early stage becomes possible by examining whether there is any deficiency in the function of FcγRIIB gene.

The present invention will now be explained more specifically with the following examples, however, the technical scope of the invention is not limited to these examples.

Reference (Generation of FcγRIIB-Deficient Mice)

A genomic DNA clone for FcγRIIB gene was isolated by screening a 129/Sv/J-lineage-derived mouse genomic DNA library. A targeting vector was constructed by replacing a 2.65 Kb fragment which includes two separate exons of $S_2$ and EC₁ of said clone to a pMC1 neo gene cassette (Toyobo Co., Ltd.). This linearized vector was introduced into ES cells (J1) by electroporation, and was homologously recombined.

The ES clone was isolated from the ES cells that were homologously recombined as mentioned above, a neomycin-resistant ES clone was screened to G418 and GANC (ganciclovir), and homologous recombinants were identified by Southern blot. Genomic DNA isolated from the identified homologous recombinants was digested with Hind III, and the existence of targeting allele containing pMC1 neo gene cassette was confirmed. The said identified ES clone was microinjected into the blastocysts to generate chimeric mice, and the generated mice were intercrossed with wild-type C57BL/6J mice to obtain heterozygous mice, then these heterozygous mice were intercrossed to obtain homozygous mice, and mice whose FcγRIIB gene is deficient on its chromosome and its wild-type mice were generated.

EXAMPLE 1

Construction of Goodpasuture's Syndrome Model Mice

A Cellmatrix IV (Nitta Gellatin, Inc.) prepared from bovine crystalline lens at 3 mg/ml protein concentration in 1 mM HCL solution (pH 3.0), was added NaOH to a final concentration of 1 mM, to generate type IV collagen (pH 8.0). Two types of emulsions were generated by mixing 3 mg/ml of said type IV collagen (pH 8.0) and 3 mg/ml of complete Freund's adjuvant (CFA) comprised of liquid paraffin, surface-active agent, and dead *Mycobacterium tuberculosis* in a connected syringe, and by mixing 3 mg/ml type IV collagen (pH 8.0) and 3 mg/ml incomplete Freund's adjuvant (IFA) comprised of liquid paraffin and surface-active agent in a connected syringe.

The FcγRIIB gene deficient mice (eight weeks of age: gender at randomly chosen) generated from the method described in the above-mentioned reference were anesthetized by ether and its tail base were shaved, and 100 μl emulsion containing 150 μg each of type IV collagen and CFA were injected to the mice's skin for primary immunization. After the primary immunization, on day 14, day 28, and day 42, 100 μl emulsion containing 150 μg each of type IV collagen and IFA were injected to their skin, the mice were killed on day 56, and the pulmonary tissues and renal tissues were extracted. In addition, wild-type mice were used as a control.

Figure 2:
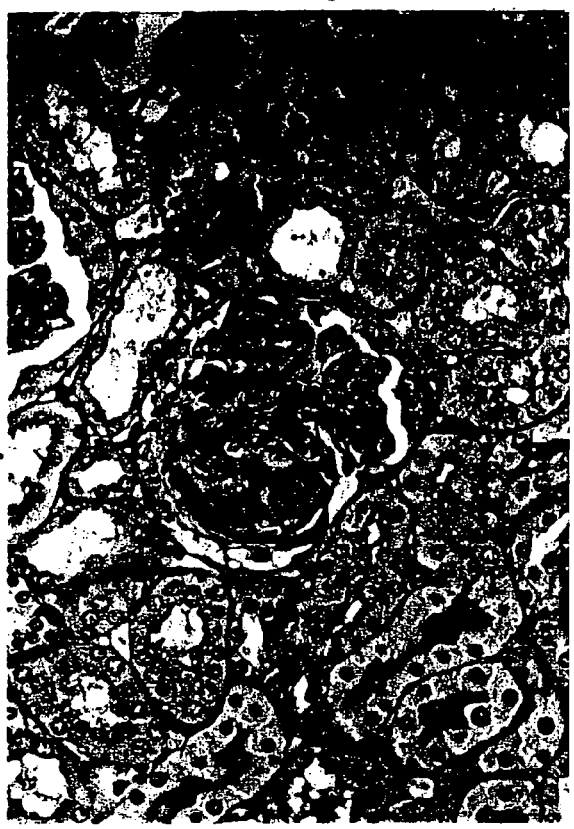
FIG. 2 is a view showing Goodpasture's syndrome-like glomerulonephritis by immunization with type IV collagen.
Figure 2:

As shown in FIG. 1, FcγRIIB gene deficient mice immunized with type IV collagen (FcγRIIB⁻/⁻), compared to control wild-type mice (WT), showed remarkable signs of alveolar hemorrhage in the pulmonary tissues at a wide range including the infiltration of inflammatory cells such as macrophages, neutrophils, and the like. In addition, as shown in FIG. 2, degeneration of glomus and proximal renal tubule in the renal tissues were displayed and renal lesion mainly as glomerulonephritis occurred. From these results, it can be understood that Goodpasuture's syndrome model mice can be obtained by immunizing FcγRIIB gene deficient mice with type IV collagen.

EXAMPLE 2

Examination of Antibody Titer to Type IV Collagen

After each of FcγRIIB knockout mice, FcRγ knockout mice, and wild-type mice were immunized with type IV collagen, blood was extracted from the orbit after a set period of time, and the antibody titer to type IV collagen was tested by the following method, where improvement had been added to the ELISA analysis previously described (Cell. Immunol. 145, 299–310, 1992).

20 μg type IV collagen was lysed in 1 ml phosphate buffered solution (PBS), and this lysate solution was used at 50μ 1/well, and after coating a 96-well microplate (Falcon; Becton Dickinson Labware) at 4° C. for overnight, was washed three times with PBS containing 0.05% Tween 20 and 0.1% BSA, and then blocked with PBS containing 0.2% BSA at 250μ 1/well at 4° C. overnight.

Figure 3:
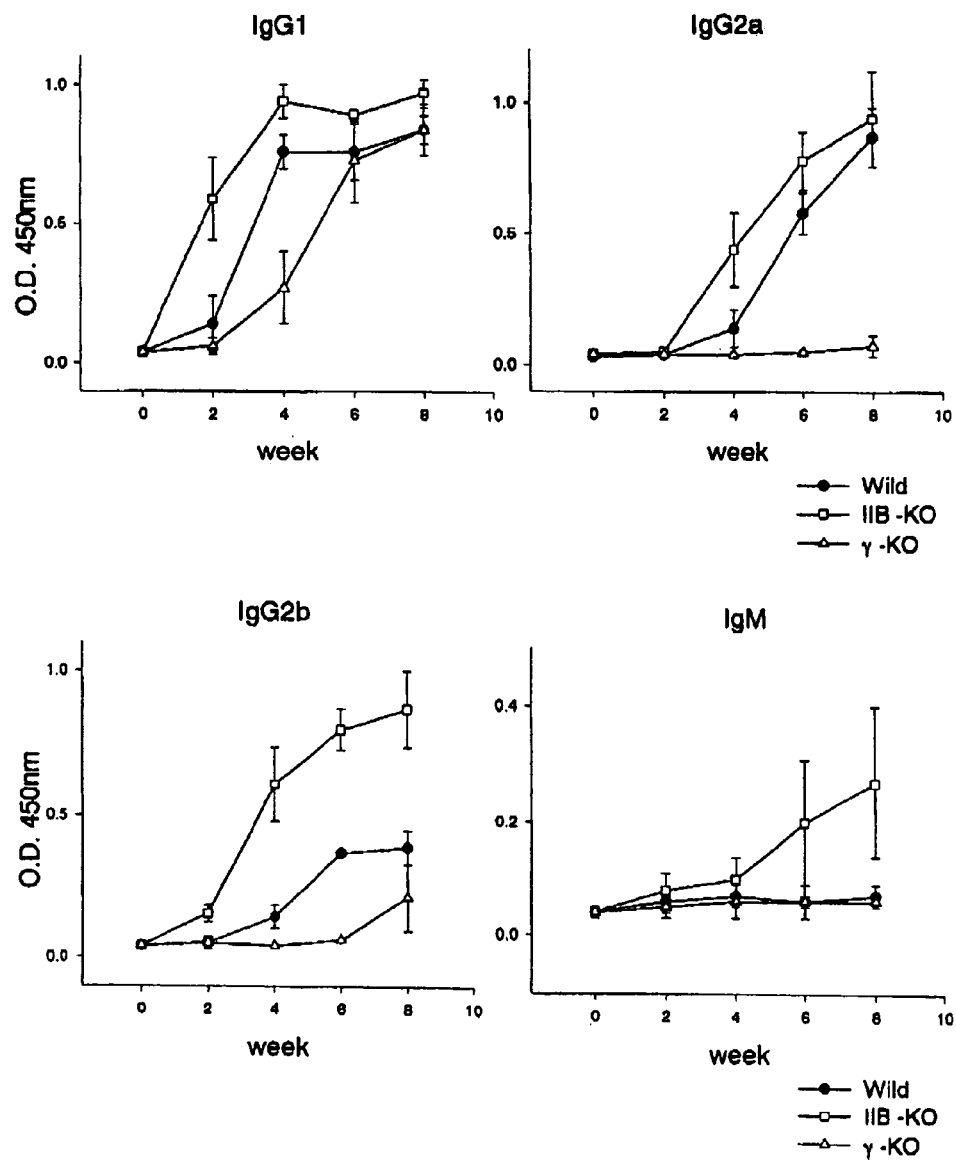
FIG. 3 is a graph showing the level of antibody titer of immunization with type IV collagen.

The serum obtained from the blood mentioned above was then diluted to 400 to 20000 times, and the diluted serum was added to the aforementioned 96-well microplate at 50μ 1/well, and allowed to react at 4° C. overnight. After the reaction, the 96-well microplate was washed three times with PBS containing 0.05% Tween 20, added 50μ 1 of horseradish peroxidase (Sigma Chemical Co.)-conjugated goat anti-mouse IgG1, IgG2a, or IgG2b diluted to 200 times, and was then incubated at 4° C. for 2 hours. After incubation, it was washed again three times with PBS containing 0.05% Tween 20, and developed enzyme reaction at room temperature for 30 minutes with 0.1 ml of True Blue Peroxidase Substrate (Kirkegaard & Perry Labs). The OD 450 was then read by using a Microplate Reader (Biolumin960; Molecular Dynamics Japan, Inc.). The results are shown in FIG. 3.

From these results, increase in antibody titer to type IV collagen (IgG1, IgG2a, IgG2b or IgM) can be seen in FcγRIIB knockout mice (IIB-KO), compared to FcRγ knockout mice (γ-KO) and wild-type mice (Wild), and since this is not inconsistent with the observations to Goodpasuture's syndrome, it was found that Goodpasture's syndrome model mouse was generated.

INDUSTRIAL APPLICABILITY

According to the present invention, a non-human model animal of Goodpasture's syndrome, a method for screening a remedy for Goodpasture's syndrome using the model animal, and a method for diagnosing Goodpasture's syndrome at the early age can be provided, which leads to the therapy of Goodpasture's syndrome, where the development of therapy had been deleyed due to the lack of adequate disease models for elucidating its onset mechanism.

What is claimed is:

1. A model mouse showing symptoms of diffuse alveolar hemorrhage, glomerulonephritis, and the appearance of antikidney glomerular basement membrane antibody, wherein the model mouse is obtained by immunizing with type IV collagen a homozygous transgenic mouse whose genome comprises a disruption of the FcγRIIB gene wherein said transgenic mouse does not produce FcγRIIB protein.

2. A method for screening a test substance for improving symptoms of diffuse alveolar hemorrhage, glomerulonephritis, and the appearance of antikidney glomerular basement membrane antibody, comprising the steps of:
   a) administering a test substance to a first model mouse showing the symptoms of diffuse alveolar hemorrhage, glomerulonephritis, and the appearance of antikidney glomerular basement membrane antibody wherein the model mouse is obtained by immunizing with type IV collagen a homozygous transgenic mouse whose genome comprises a disruption of the FcγRIIB gene wherein said transgenic mouse does not produce FcγRIIB protein, b) determining at least one symptom selected from the group consisting of diffuse alveolar hemorrhage, glomerulonephritis, and the appearance of antikidney glomerular basement membrane antibody, c) performing a comparative evaluation with a second model mouse used as control to which the test substance is not administered, wherein a decrease in the severity of at least one said symptom in the first model mouse to which the test substance is administered compared to the second model mouse to which the test substance is not administered indicates that the test substance is effective to improve said symptom.

* * * * *

UNITED STATES PATENT AND TRADEMARK OFFICE
CERTIFICATE OF CORRECTION

PATENT NO. : 7,135,607 B1
APPLICATION NO. : 10/009950
DATED : November 14, 2006
INVENTOR(S) : Nakamura et al.

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by (364) days Delete the phrase "by 364" and insert -- by 657 days--

Signed and Sealed this

Sixth Day of March, 2007

JON W. DUDAS
*Director of the United States Patent and Trademark Office*